(12) United States Patent
Tsumura et al.

(10) Patent No.: US 9,211,399 B2
(45) Date of Patent: Dec. 15, 2015

(54) DISPOSABLE ELECTRODE AND AUTOMATIC INFORMATION RECOGNITION APPARATUS

(75) Inventors: Ikuhiro Tsumura, Tokyo (JP); Hiroyuki Nishiyama, Tokyo (JP); Yuji Igawa, Tokyo (JP); Yohiyuki Hamauzu, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 63 days.

(21) Appl. No.: 12/558,464

(22) Filed: Sep. 11, 2009

(65) Prior Publication Data

US 2010/0070011 A1   Mar. 18, 2010

(30) Foreign Application Priority Data

Sep. 12, 2008 (JP) ................. 2008-234955

(51) Int. Cl.
*A61N 1/08*   (2006.01)
*A61N 1/04*   (2006.01)

(52) U.S. Cl.
CPC .............. *A61N 1/046* (2013.01); *A61N 1/0492* (2013.01)
USPC ..................................................... 607/142

(58) Field of Classification Search
CPC ....... A61N 1/0404; A61N 1/046; A61N 1/06; A61N 1/36014; A61N 1/3625; A61N 1/38; A61N 1/39; A61N 1/3993; A61N 1/0492
USPC ..................................... 607/5, 142
See application file for complete search history.

(56) References Cited

U.S. PATENT DOCUMENTS

| | | |
|---|---|---|
| 2003/0055478 A1 | 3/2003 | Lyster et al. |
| 2009/0326632 A1* | 12/2009 | Craige et al. .................. 607/142 |
| 2010/0023074 A1* | 1/2010 | Powers et al. .................... 607/5 |
| 2010/0174332 A1* | 7/2010 | Vaisnys et al. .................... 607/5 |

FOREIGN PATENT DOCUMENTS

| | | |
|---|---|---|
| JP | 58-111163 A | 7/1983 |
| JP | 58-215747 A | 12/1983 |
| JP | 8-168536 A | 7/1996 |
| JP | 2001-218854 A | 8/2001 |
| JP | 2006-275724 A | 10/2006 |
| JP | 2006-275923 A | 10/2006 |
| WO | 2006/102420 A2 | 9/2006 |
| WO | 2006102420 A | 9/2006 |

OTHER PUBLICATIONS

Extended European Search Report Nov. 18, 2009.
Japanese Office Action for related Japanese Patent Application No. 2008-234955 dated Jul. 6, 2012.
Japanese Office Action for related Japanese Patent Application No. 2008-234955 dated Sep. 25, 2012.

* cited by examiner

*Primary Examiner* — Christopher D Koharski
*Assistant Examiner* — Frances Oropeza
(74) *Attorney, Agent, or Firm* — Kenealy Vaidya LLP

(57) ABSTRACT

A disposable electrode includes: an electrode pad; and a connector, connecting the electrode pad to a defibrillator, and including an information holder that can be provided with a transmissive opening or a light reflective member, the information holder holding information about at least an expiration date, depending on presence or absence of the transmissive opening or the light reflective member, the information holder allowing the information to be notified from the defibrillator when the connector is connected to the defibrillator.

5 Claims, 7 Drawing Sheets

DISPOSABLE ELECTRODE AND AUTOMATIC INFORMATION RECOGNITION APPARATUS

BACKGROUND OF THE INVENTION

The present invention relates to a disposable electrode which is to be used in a defibrillator, and in which the expiration date of the disposable electrode can be recognized, and also to an automatic information recognition apparatus for the disposable electrode.

In a defibrillator such as an automatic external defibrillator (AED), a disposable electrode is used to facilitate miniaturization and portability. A disposable electrode uses a gel material at a portion of the electrode which is to be contacted with a patient's body. When the gel is dried, the disposable electrode cannot be used. Therefore, a disposable electrode is stored in a state where it is placed in a sealed container. However, such a gel deteriorates with time, and has a possibility of changing to an electrical state which is not adequate as an electrode. Therefore, an expiration date is defined, and printed on the sealed container or the like.

The user must check the printed expiration date, and prepare a disposable electrode which has not passed the expiration date. In a defibrillator, moreover, also a training electrode is used in order to conduct practice training to provide for an emergency. In the case where a training electrode is connected to a defibrillator, the operation sequence is not advanced until a regular electrode is connected, from the viewpoint of avoiding the risk.

In the present state of the art of defibrillators and their electrodes, unless the user pays adequate attention, it is impossible to eliminate the possibility that, in case of emergency, a situation occurs where the expiration date has been passed, or where a training electrode remains connected to a defibrillator.

By contrast, a defibrillator is known which includes a plurality of coupling points that, when an electrode connector is connected to a main-unit connector, can recognize the type of the electrode. Such a defibrillator is configured so as to detect also that an electrode is not connected thereto (JP-A-8-168536, particularly see paragraphs 0017 to 0020).

Moreover, also a defibrillation electrode is known in which a connector for the electrode includes an internal use paddle electrode and an adhesive type electrode includes an identifying signal producing circuit that is configured by a resistor, and that produces an identifying signal indicative of an internal electrode (see FIG. 9 and paragraph 0024 of JP-A-2001-218854).

Furthermore, also a biosensor is known in which information including an expiration date is stored in an IC tag or a memory element, and the information is read out by a reading apparatus (see JP-A-2006-275724 and JP-A-2006-275923).

Furthermore, it is contemplated that, in an electrode-side connector which connects an electrode to a defibrillator main unit, a semiconductor device such as a memory element for storing an expiration date and the type of the electrode is disposed.

In the connector disclosed in JP-A-8-168536, when the amount of information is to be increased, the coupling points must be increased, and there is a possibility that the size or the production cost is increased by the augmented configuration. The circuit disclosed in JP-A-2001-218854 is configured by a resistor, and hence the accuracy is problematic. Moreover, there is a possibility that erroneous recognition occurs due to a temporal change or a temperature change of the resistance.

The IC tag or memory element disclosed in JP-A-2006-275724 and JP-A-2006-275923 is relatively expensive, and hence is not appropriate for the use in a disposable electrode. There is a further problem in that the reading apparatus has a relatively large-scaled configuration.

In the configuration in which a resistor, a semiconductor device, or the like is disposed in a connector, an electrical component such as the resistor or the semiconductor device must be placed in a narrow place. In disposition of an electrical component, a phenomenon that an unexpected voltage is applied to a patient body by, for example, contacting the component with another terminal must be definitely avoided. Therefore, the configuration and cost for avoiding the phenomenon are inevitably increased.

SUMMARY

It is therefore an object of the invention to provide a disposable electrode in which there is no possibility of a temporal change or a temperature change, the size and the production cost are not increased even when the amount of information is to be increased, the configuration of a reading apparatus can be made relatively small, and an electrical component is not required to be used in an electrode-side connector, and also to provide an automatic information recognition apparatus for the disposable electrode.

In order to achieve the object, according to the invention, there is provided a disposable electrode comprising:

an electrode pad; and a connector, connecting the electrode pad to a defibrillator, and including an information holder that can be provided with a transmissive opening or a light reflective member, the information holder holding information about at least an expiration date, depending on presence or absence of the transmissive opening or the light reflective member, the information holder allowing the information to be notified from the defibrillator when the connector is connected to the defibrillator.

The information held in the information holder may include information indicative of whether the connector is properly connected to the defibrillator or not.

The information held in the information holder may include information indicative of an electrode type, or whether the disposable electrode is a training electrode or an actual electrode.

According to the invention, there is also provided an automatic information recognition apparatus for the disposable electrode, the automatic information recognition apparatus comprising:

a detecting unit, detecting presence or absence of the transmissive opening or the light reflective member, which is provided with the information holder of the connector, and generating a signal, in a state where the connector is connected to the defibrillator;

a notifying unit, notifying the information held in the information holder; and a controlling unit, based on the signal from the detecting unit, obtaining the information, and causing the notifying unit to notify the information.

The detecting unit may comprise a light source and a light receiving element which are placed in the defibrillator so that presence or absence of the transmissive opening or the light reflective member, which is provided with the information holder of the connector, can be detected in a state where the connector is properly connected to the defibrillator.

DETAILED DESCRIPTION OF EMBODIMENTS

Figure 1:
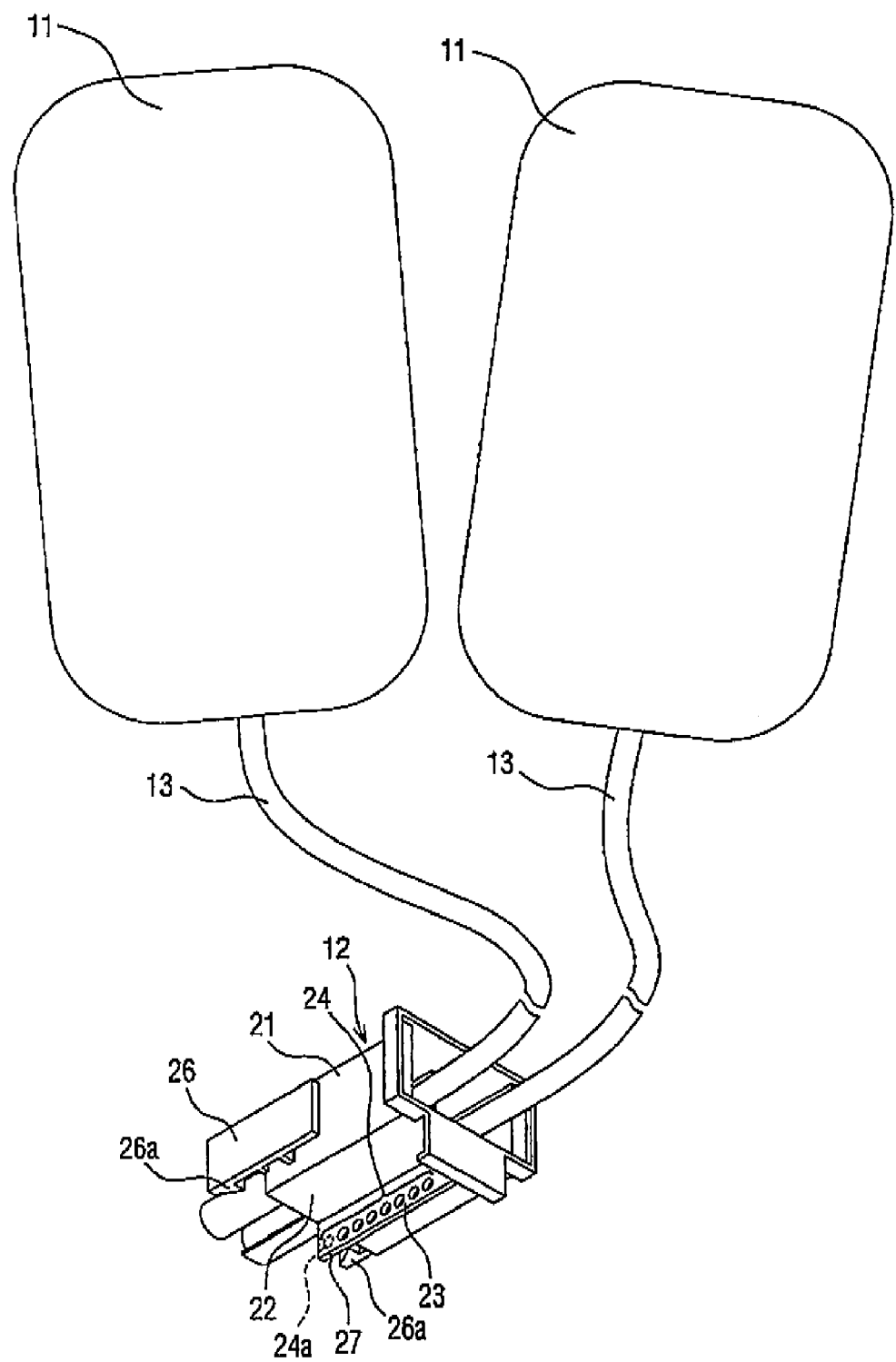
FIG. 1 is a perspective view of a configuration showing a disposable electrode that includes a connector according to the present invention.
Figure 2:
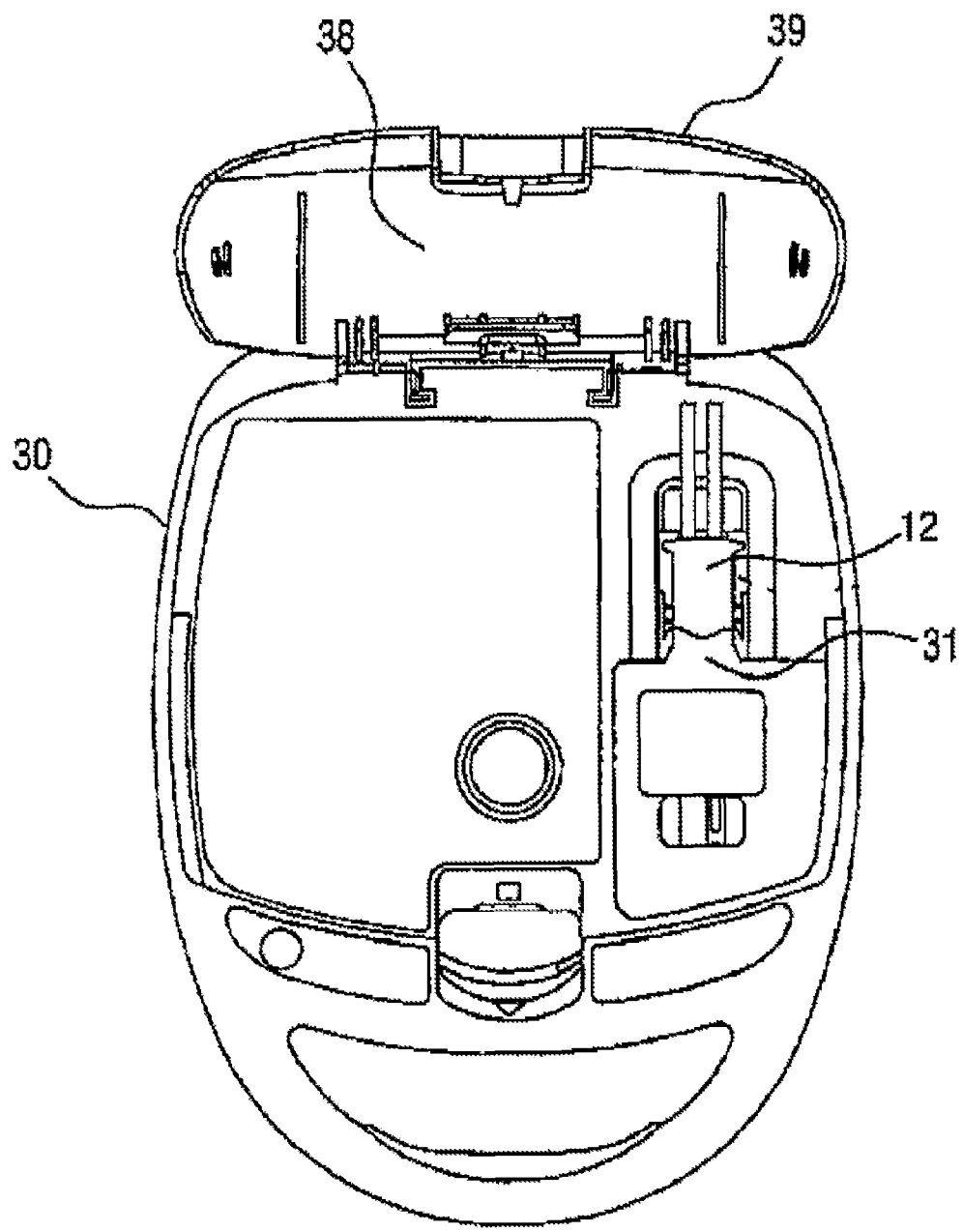
FIG. 2 is a plan view showing a state where the connector is incorporated into a defibrillator.

Hereinafter, a disposable electrode of the present invention and an automatic information recognition apparatus for the electrode of the invention will be described with reference to FIGS. 1 to 6 of the accompanying drawings. In the figures, identical components are denoted by the same reference numerals, and duplicated description is omitted. As shown in FIG. 1, a disposable electrode which is to be used in a defibrillator has a configuration where two electrode pads 11 and a connector 12 are connected to each other by two cables 13. The two electrode pads 11 are hermetically sealed together with half portions of the two cables in a pouch. In a defibrillator 30 which is shown in FIG. 2 in a state where a lid 39 is opened, the pouched electrode pads 11 are placed in an electrode accommodating portion 38 on the back (inner) side of the lid 39, while the connector 12 is connected to a connector 31 of the defibrillator 30.

In the connector 12, a planar fin 27 is disposed on a face 22 which is the lower face of a rectangular parallelepiped connector chassis 21 in the use state. The fin 27 is vertically projected from the lower face 22, and extends in a direction along which the connector 12 is connected to the connector 31 of the defibrillator 30. The fin 27 includes an information holding portion 23.

The information holding portion 23 includes eight circular transmissive openings that can be opened at predetermined opening positions 24, respectively. The portion 23 can hold 8-bit information whereby one of the openings is opened and is set to "1", and whereby one of the openings is not opened and is set to "0". In one embodiment, the following three kinds of information are held by the information holding portion 23. Namely, information indicative of the expiration date of the disposable electrode is held in the opening positions of six transmissive openings which are continuously arranged starting from the side of the cables 13, electrode kind information indicative of whether the disposable electrode is a training electrode or an actual electrode is held in the next one opening position, and connection information indicative of whether the connector 12 is properly connected to the connector 31 of the defibrillator 30 or not is held in the further next one opening position.

Figure 6:
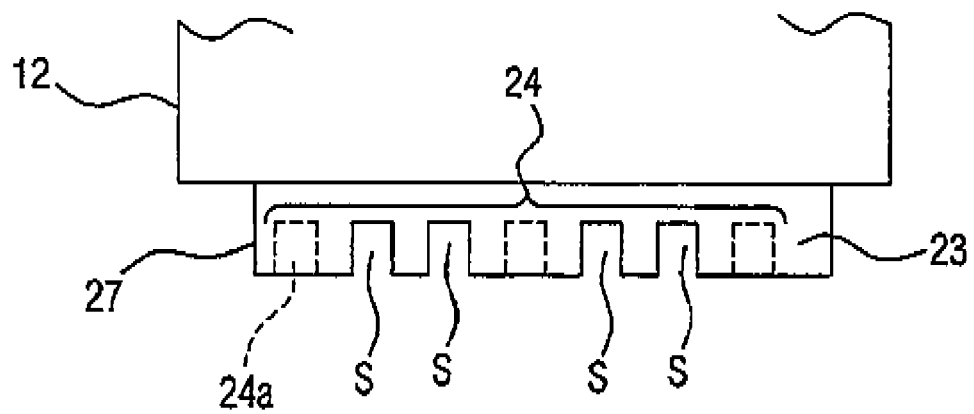
FIG. 6 is a plan view showing an example of transmissive openings which are opened in an information holding portion.

In the embodiment, the eight circular transmissive openings can be opened in the information holding portion 23. Depending on the amount of information, the number of the transmissive openings can be increased or decreased. The transmissive openings are not restricted to be circular, and, for example, may be configured as slits S as shown in FIG. 6. Such slits are within the scope of the transmissive openings. One bit is allocated to the electrode kind information. In a training electrode, the expiration date information is not necessary, and hence a special bit pattern in which, for example, all the transmissive openings are not opened may be formed. According to the configuration, the opening for the electrode kind information is not required.

The opening positions of the transmissive openings respectively corresponding to the expiration date information and the electrode kind information are in the state where the transmissive openings are opened or not opened in accordance with the respective information. The opening position of the transmissive opening corresponding to the connection information is an opening position 24a which is located at the tip end in the direction along which the connector 12 is connected to the connector 31 of the defibrillator 30, and the transmissive opening is not opened because, in the case where the connectors 21 and 31 are incompletely connected to each other, nothing interrupts between a light source and light receiving element which will be described later.

Figure 4:
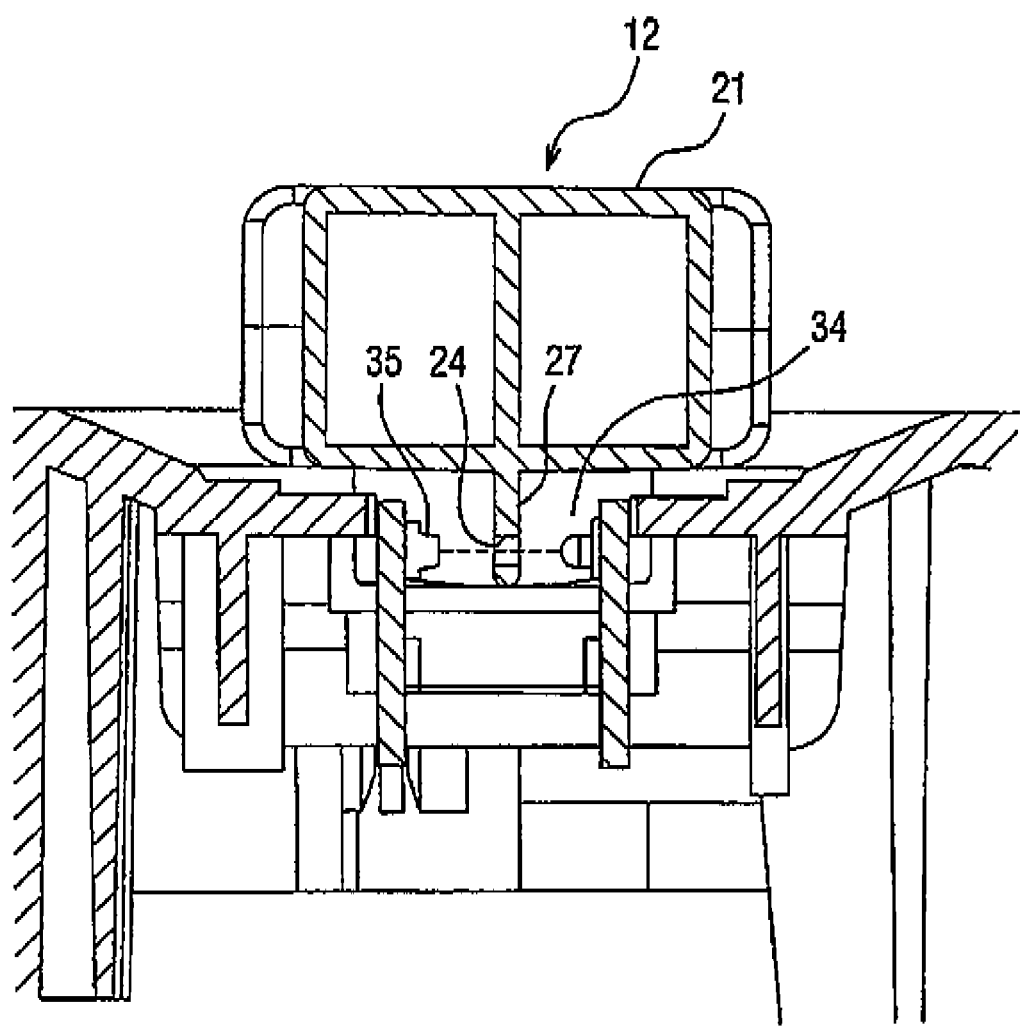
FIG. 4 is an A-A sectional view of FIG. 3.

As shown in FIG. 4, the defibrillator 30 includes eight light emitting diodes (LEDs) 34 which function as the light source, and eight photodiodes 35 which function as the light receiving element. In a state where the connector 12 is properly connected to the connector 31 of the defibrillator 30, respective pairs of the LEDs 34 and the photodiodes 35 are opposed to each other across the respective opening positions of the eight openings of the information holding portion 23. The number of the LEDs 34 or the like constituting the light source may be smaller than that of the opening positions 24 of the transmissive openings, as far as emission light which has been passed through the opened transmissive opening has a light intensity that can be sufficiently received by the light receiving element such as the photodiode 35 corresponding to the transmissive opening.

Figure 3:
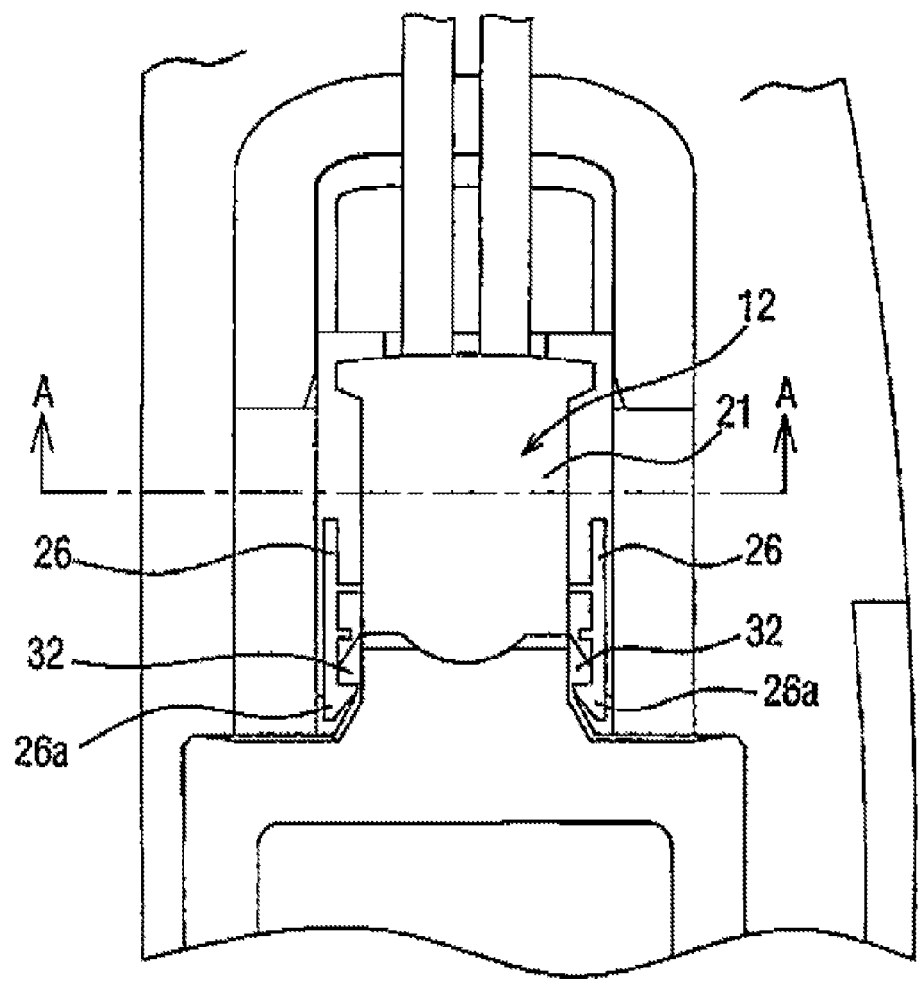
FIG. 3 a plan view enlargedly showing the connector.

As shown in FIG. 3, clamping arms 26 which maintain the connection state between the connector 12 and the connector 31 of the defibrillator 30 are disposed on the pair of side walls of the connector 12, and claw portions 26a which are inward bent are formed on the tip ends of the clamping arms 26, respectively By contrast, engagement projections 32 are formed on the defibrillator 30. When the connector 12 is properly connected to the connector 31, the claw portions 26a and the engagement projections 32 are engaged with each other to maintain the connection state of the connectors 12 and 31. In the connection state, the eight LEDs 34 and the eight photodiodes 35 are just opposed to the opening positions 24 of the corresponding transmissive openings, respectively, and the information of the disposable electrode can be detected on the basis of light intensities which are detected by the photodiodes 35 in accordance with the opening states of the transmissive openings.

Figure 5:
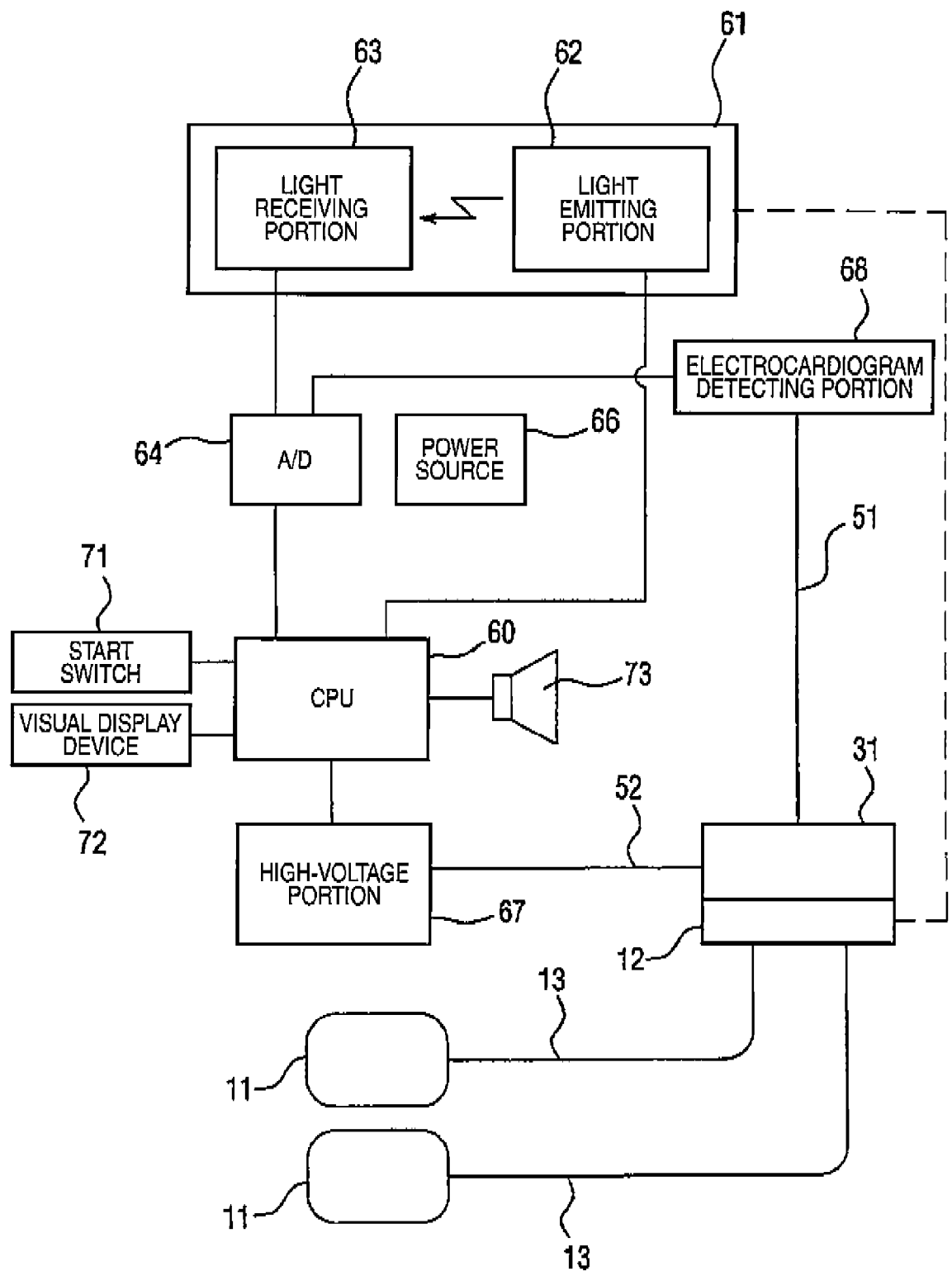
FIG. 5 is a circuit block diagram showing an automatic expiration date recognition apparatus for the disposable electrode of the invention.

FIG. 5 shows the circuit configuration of an automatic external defibrillator including an automatic expiration date recognition apparatus for the disposable electrode of the embodiment. From the connector 31 of the defibrillator 30 connected to the connector 12 which is connected to the two electrode pads 11 through the cables 13, a signal line 51 extends to an electrocardiogram detecting portion 68 for detecting an electrocardiogram, and a high-voltage supply line 52 for supplying a high voltage to the electrode pads 11 extends to a high-voltage portion 67 for generating the high voltage to be applied to the electrode pads 11.

The reference numeral 61 denotes a detecting portion which detects the information of the disposable electrode that is held by the information holding portion 23 of the connector 12. The detecting portion has a light emitting portion 62 including the eight LEDs 34, and a light receiving portion 63 including the eight photodiodes 35, and the information holding portion 23 which is formed in the above-described fin 27 is placed between the light emitting portion 62 and the light receiving portion 63. The light emitting portion 62 controls the LEDs 34 so as to emit light in accordance with an instruction signal supplied from a CPU 60, and a signal corresponding to the opened and unopened transmissive openings which are formed in the information holding portion 23 is obtained from the light receiving portion 63. The signal is sent to an A/D converter 64.

The A/D converter 64 converts the analog signal to a digital signal, and sends the digital signal to the CPU 60. In addition to the A/D converter 64 a start switch 71 for applying the high voltage for defibrillation to a patient body through the electrode pads 11, a visual display device 72, a speaker 73 for producing an audio announcement, and the high-voltage portion 67 are connected to the CPU 60. The output of the electrocardiogram detecting portion 68 is supplied to the A/D converter 64. A power source 66 supplies electrical power to the components.

The operation of the thus configured automatic external defibrillator including the automatic expiration date recognition apparatus for the disposable electrode of the embodiment will be described. When a power supply switch (not shown) is turned on, the operation for defibrillation is started. The CPU 60 displays the status of the apparatus and a guide for operation on the visual display device 72, and outputs sounds of an operation guides and the like from the speaker 73. Based on the electrocardiogram supplied from the A/D converter 64, the CPU determines whether defibrillation is necessary or not, and, in accordance with the result of the determination, outputs required information from the visual display device 72 and the speaker 73. If it is determined that defibrillation is necessary, the CPU controls the high-voltage portion 67 so as to generate the high voltage for defibrillation. The above-described operations are identical with those of a related-art automatic external defibrillator.

Next, automatic recognition of the information of the disposable electrode held by the information holding portion 23 will be described. A circuit for automatic recognition is activated by a timer (not shown), at predetermined time intervals, or at a predetermined time, once a day, and the information held by the information holding portion 23 is automatically recognized and then notified. The CPU 60 receives the signal which is obtained by the light receiving portion 63, and which corresponds to the opened and unopened transmissive openings at the opening positions 24 of the information holding portion 23, from the A/D converter 64. Based on the signal (8 bits), the CPU detects whether the connector 12 is properly connected to the connector 31 of the defibrillator 30 or not, detects the expiration date, detects the electrode kind indicating whether the electrode is a training electrode or an actual electrode, and notifies the information through the visual display device 72 and the speaker 73.

If it is detected that the connector 12 is not properly connected to the connector 31 of the defibrillator 30, there is a possibility that the detections of the expiration date and the electrode kind are disabled or erroneously performed, and hence the expiration date and the electrode kind are not detected. In the case where the connection state between the connector 12 and the connector 31 of the defibrillator 30 is not adequate, an alarm such as "Connector is disconnected" is issued through the visual display device 72 and the speaker 73.

If it is detected that the connector 12 is properly connected to the connector 31 of the defibrillator 30, the CPU 60 detects the expiration date and the electrode kind, and supplies their information to the visual display device 72 and the speaker 73 to be output therefrom. The expiration date information to be output may be the expiration date itself in terms of the year and month, or the period before the expiration date may be expressed as "XX years and YY months before expiration date". With respect to the output of the electrode kind, in the case where a training electrode is connected, alert information such as "Training electrode is connected" is output through the visual display device 72 and the speaker 73.

As described above, the connection state between the connector 12 and the connector 31, the expiration date of the disposable electrode, and the electrode kind can be automatically checked at predetermined time intervals, or at a predetermined time, once a day. Since the configuration where presence or absence of the transmissive openings is detected by means of light is employed, a temporal change which may occur if a contact is eliminated, and hence stable and accurate inspection is enabled.

In the above description, inspection is performed by using the timer at predetermined time intervals, or at a predetermined time, once a day. Alternatively, an inspection switch may be additionally disposed, and inspection may be performed at an arbitrary timing, or inspection may be performed at a required timing such as when the lid 39 of the defibrillator 30 is opened. Furthermore, these inspection methods may be combined with each other.

Figure 7:
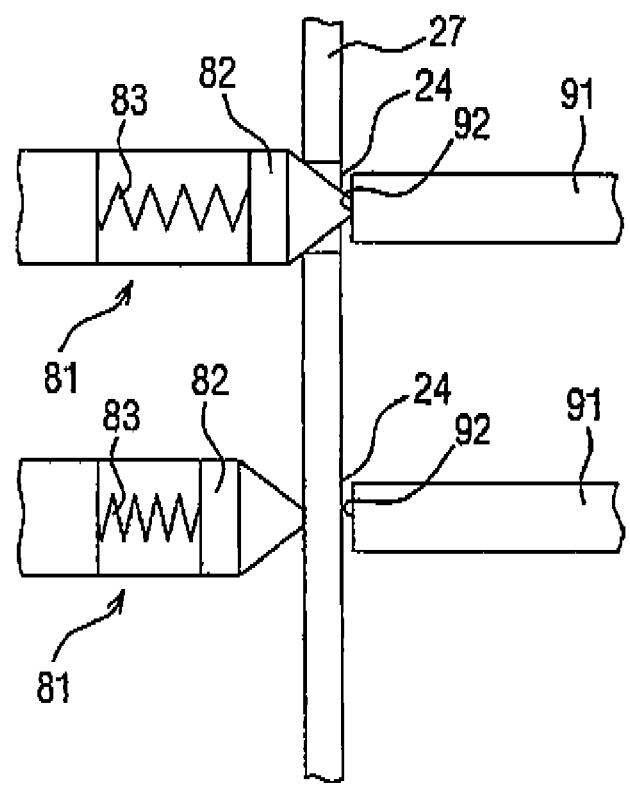
FIG. 7 is a sectional view showing the configuration of a detecting unit in a second mode of carrying out the disposable electrode and the automatic expiration date recognition apparatus for the electrode of the invention.

Next, a second mode of carrying out the invention will be described with reference to FIG. 7. The mode is different only in the unit for detecting presence or absence of the transmissive openings, from the above-described mode. Therefore, identical components are denoted by the same reference numerals, and duplicated description is omitted. As shown in FIG. 7, the unit for detecting presence or absence of the transmissive openings has a configuration where movable portions 81 each including a contact 82 which is projected by a spring 83, and detecting portions 91 each including a stationary contact 92 which is to be contacted with the projected contact 82 are opposed to each other across the fin 27 and the opening positions 24 of the corresponding transmissive openings, and a contact of one of the movable portions 81 and the corresponding one of the detecting portions 91 is detected by a current flow. When one of the transmissive openings is opened, the corresponding contact 82 is contacted with the corresponding stationary contact 92, and, when the transmissive opening is not opened, the contact 82 is not contacted with the stationary contact 92.

Figure 8:
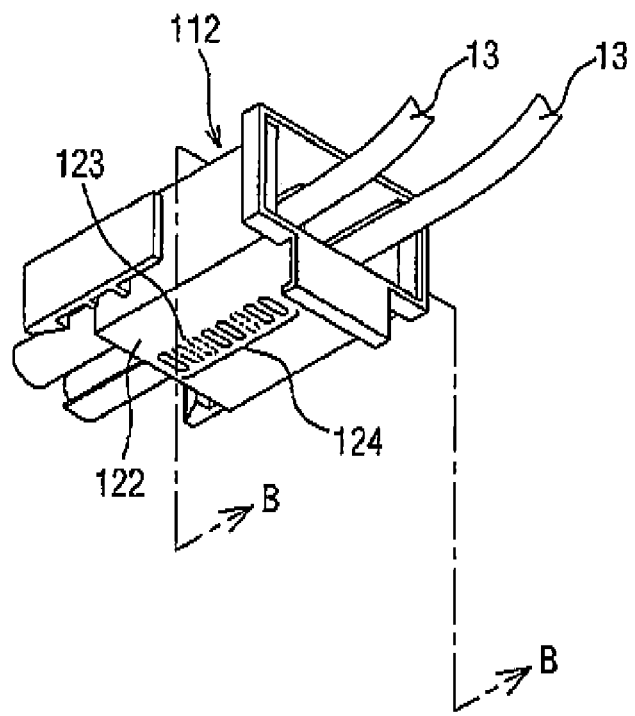
FIG. 8 is a perspective view of a connector in a third mode of carrying out the disposable electrode and the automatic expiration date recognition apparatus for the electrode of the invention.
Figure 9:
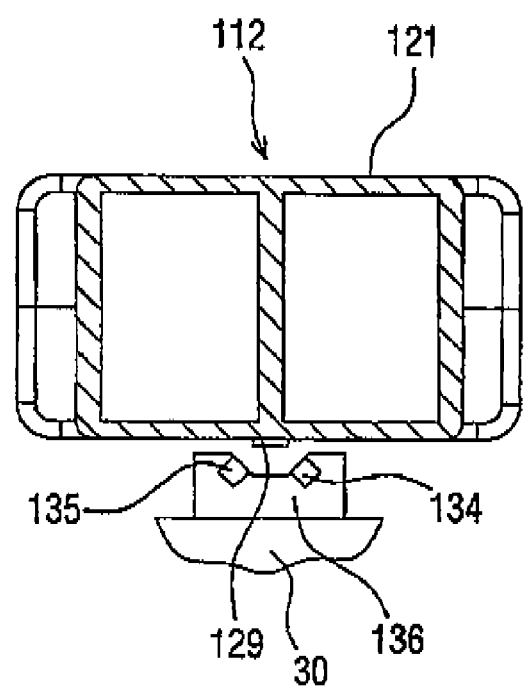
FIG. 9 is a B-B sectional view of FIG. 8.

Next, a third mode of carrying out the invention will be described with reference to FIGS. 8 and 9. This mode is different only in the information holding portion which holds information of the disposable electrode, and the unit for detecting information of the information holding portion, from the above-described mode. Therefore, identical components are denoted by the same reference numerals, and duplicated description is omitted. FIG. 8 is a perspective view of a connector 112 of a disposable electrode, and FIG. 9 is a B-B sectional view of FIG. 8. An information holding portion 123 is disposed on the lower face 122 of the connector 112 of the disposable electrode, and configured so that eight reflective stickers 129 functioning as a light reflective member are bonded to bond positions 124, respectively. For example, the information holding portion 123 and the vicinity thereof have a structure which is colored black and hardly reflective. By contrast, each of the reflective stickers 129 is a circular thin sticker having a smooth surface and a color in which reflection easily occurs, such as white or silver, and can be bonded to one of the reflective sticker bond positions 124 by a cohesive agent or an adhesive agent. The information holding portion can hold 8-bit information while, for example, the state where one of the reflective stickers 129 is bonded is set to "1", and that where one of the reflective stickers 129 is not bonded is set to "0". In place of bonding of the reflective stickers 129, one sticker on which a reflective/non-reflective pattern corresponding to information to be held is previously printed may be bonded in accordance with the bond positions 124.

With respect to the information to be held by the information holding portion 123 of a chassis 121 and its position in the embodiment, the expiration date information, the electrode kind information, and the connection information are arranged starting from the side of the cables 13 in the same manner as the above-described mode. The connection information is configured by bonding of the reflective sticker 129 because, in the case where the connectors 112 and 31 are incompletely connected to each other, the light receiving element cannot receive light from the light source which will be described later.

As shown in FIG. 9, the defibrillator 30 has eight reflective photo-interrupters 136. In each of the reflective photo-interrupters 136, an LED 134 which functions as the light source, and a phototransistor 135 which functions as the light receiving element are integrated with each other. The phototransistor 135 receives reflected light of the light emitted from the LED 134 to detect an article. The reflective photo-interrupters 136 are arranged so as to correspond respectively to the eight reflective sticker bond positions 124 of the information holding portion 123 in a state where the connector 112 is properly connected to the connector 31 of the defibrillator 30. When the reflective sticker 129 is bonded to the bond position 124, the light emitted from the LED 134 is reflected by the reflective sticker 129, and then received by the phototransistor 135.

In the embodiment, automatic recognition of the information of the disposable electrode which is held by the information holding portion 123 is performed in a similar manner as the above-described mode.

According to the disposable electrode of the invention, the information holding portion is configured so that a plurality of transmissive openings or light reflective members are able to be disposed in a chassis of the connector, and, depending on presence or absence of the transmissive openings or the light reflective members, information about at least an expiration date is held. Therefore, effects are achieved where there is no possibility of a temporal or temperature change, and the size and the production cost are hardly increased.

When employing the configuration where information indicative of whether the connector is properly connected to the defibrillator or not is held in the information holding portion, it is possible to surely notify an occurrence of incomplete connection in the case where the disposable electrode is connected to the defibrillator.

When employing the configuration where information indicative of an electrode type, or whether the disposable electrode is a training electrode or an actual electrode is held in the information holding portion, it is possible to monitor whether the disposable electrode is a training electrode or an actual electrode. Therefore, a situation where an incorrect kind of disposable electrode is used can be prevented from occurring.

In the automatic information recognition apparatus for a disposable electrode of the invention, on the basis of the signal detected by the detecting unit for detecting presence or absence of the transmissive openings or light reflective members of the information holding portion in the state where the connector of the disposable electrode is connected to the defibrillator, information of the disposable electrode is obtained, and then notified. Therefore, effects are achieved where there is no possibility of a temporal or temperature change, and the size and the production cost are hardly increased. Furthermore, the information holding portion is configured without using any electrical component. Even when the disposable electrode is connected to the defibrillator, therefore, a phenomenon that an unexpected voltage due to the information holding portion is applied to a patient body never occurs. Also in this viewpoint, the configuration and the cost are not increased.

The apparatus obtains information of the disposable electrode, based on receiving/non-receiving signals obtained from the light source and light receiving element which are placed in the defibrillator so that presence or absence of the transmissive openings or light reflective members of the information holding portion can be detected in the state where the connector is properly connected to the defibrillator. Therefore, there is no possibility of a temporal or temperature change, and the size and the production cost are hardly increased even when the amount of information is to be increased. As to the light source and the light receiving element, a light emitting diode and a photodiode can be used, so that the detecting unit can be maintained to have a relative small configuration. Moreover, no electrical contact is used, and hence the reliability is enhanced.

What is claimed is:

1. A disposable electrode comprising:
   an electrode pad; and
   a connector, connecting the electrode pad to a defibrillator, and including an information holder configured to be provided with one or more transmissive openings or light reflective members, the information holder holding information about at least an expiration date based upon a presence or absence of the transmissive openings or the light reflective members, and the information holder being configured to allow the information to be communicated to a CPU for providing an output from the defibrillator when the connector is connected to the defibrillator.

2. The disposable electrode according to claim 1, wherein, the information held in the information holder includes information indicative of whether the connector is properly connected to the defibrillator or not.

3. The disposable electrode according to claim 1, wherein, the information held in the information holder includes information indicative of an electrode type, or whether the disposable electrode is a training electrode or an actual electrode.

4. An automatic information recognition apparatus comprising:
   the disposal electrode according to claim 1;
   a detecting unit, detecting presence or absence of the transmissive opening or the light reflective member, which is provided with information from the information holder of the connector, and generating a signal, in a state where the connector is connected to the defibrillator;
   a notifying component, configured to communicate the information held in the information holder;
   wherein the CPU, based on the signal from the detecting unit, obtains the information, and causes the notifying unit to communicate the information to at least one of the visual display and the audio device.

5. The automatic information recognition apparatus according to claim 4, wherein the detecting unit comprises a light source and a light receiving element which are placed in the defibrillator so that presence or absence of the transmissive opening or the light reflective member can be detected in a state where the connector is properly connected to the defibrillator.

\* \* \* \* \*